United States Patent
Kalhapure et al.

(10) Patent No.: US 11,382,863 B2
(45) Date of Patent: Jul. 12, 2022

(54) INJECTABLE SUSPENSION COMPRISING AN INSOLUBLE CORTICOSTEROID AND A SOLUBLE CORTICOSTEROID

(71) Applicant: Somerset Therapeutics LLC, Hollywood, FL (US)

(72) Inventors: Rahul Kalhapure, Somerset, NJ (US); Prem Sagar Akasapu, Somerset, NJ (US); Veerappan Subramanian, Somerset, NJ (US); Ilango Subramanian, Somerset, NJ (US)

(73) Assignee: Somerset Therapeutics LLC, Hollywood, FL (US)

( * ) Notice: Subject to any disclaimer, the term of this patent is extended or adjusted under 35 U.S.C. 154(b) by 0 days.

(21) Appl. No.: 17/192,570

(22) Filed: Mar. 4, 2021

(65) Prior Publication Data

US 2021/0275451 A1    Sep. 9, 2021

Related U.S. Application Data

(60) Provisional application No. 62/984,983, filed on Mar. 4, 2020.

(51) Int. Cl.
*A61K 9/10* (2006.01)
*A61K 31/573* (2006.01)
*A61K 9/00* (2006.01)

(52) U.S. Cl.
CPC .............. *A61K 9/10* (2013.01); *A61K 9/0019* (2013.01); *A61K 31/573* (2013.01)

(58) Field of Classification Search
None
See application file for complete search history.

(56) References Cited

U.S. PATENT DOCUMENTS

| | | | | |
|---|---|---|---|---|
| 9,833,460 | B2 * | 12/2017 | Shah | A61K 47/36 |
| 2018/0250312 | A1 * | 9/2018 | Kandavilli | A61K 47/10 |
| 2019/0269616 | A1 * | 9/2019 | Pramanick | A61K 31/57 |

OTHER PUBLICATIONS

Pharma Pathway (https://pharmapathway.com/qualification-of-nitrogen-gas-producing-system-in-pharmaceuticals/). (Year: 2017).*
FDA (https://www.accessdata.fda.gov/drugsatfda_docs/label/2008/014602s047lbl.pdf) (Year: 2008).*

* cited by examiner

*Primary Examiner* — Celeste A Roney
(74) *Attorney, Agent, or Firm* — William D. Hare, Esq.; McNeely, Hare & War, LLP

(57) ABSTRACT

The present invention relates to a process for preparation of an insoluble corticosteroid and a soluble corticosteroid composition by moist heat sterilization and homogenization. In particular, the invention relates to a process for the preparation of a sterilized suspension of betamethasone acetate and betamethasone sodium phosphate, wherein the process comprises sterilizing a slurry of the betamethasone acetate by moist heat sterilization or autoclaving in about 30% to about 70% of water to a temperature of about 115° C. to about 128° C. for about 15 minutes to about 60 minutes under nitrogen atmosphere. The suspensions prepared by using the current invention exhibited good physical and chemical stability. Compositions related thereto are also disclosed.

20 Claims, 2 Drawing Sheets

```
┌─────────────────────────────────────────────────────────────────┐
│ Disperse weighed quantity of betamethasone acetate in WFI (30 to 70%). │
│                (Dissolved oxygen level NMT 2 ppm).              │
└─────────────────────────────────────────────────────────────────┘
                                ⇩
┌─────────────────────────────────────────────────────────────────┐
│ Sterilize the slurry in a mixing condition at 122°C in between 15 to 60 │
│              minutes under nitrogen atmosphere.                 │
└─────────────────────────────────────────────────────────────────┘
                                ⇩
┌─────────────────────────────────────────────────────────────────┐
│        Allow the slurry to cool to room temperature under stirring. │
└─────────────────────────────────────────────────────────────────┘
                                ⇩
┌─────────────────────────────────────────────────────────────────┐
│ Prepare a solution of betamethasone sodium phosphate, dibasic   │
│ sodium phosphate dihydrate, monobasic sodium phosphate dihydrate, │
│ edetate disodium, and benzalkonium chloride in WFI in tank 2.   │
└─────────────────────────────────────────────────────────────────┘
                                ⇩
┌─────────────────────────────────────────────────────────────────┐
│ Transfer this aqueous solution through a 0.22 μm filter to tank 1. │
└─────────────────────────────────────────────────────────────────┘
                                ⇩
┌─────────────────────────────────────────────────────────────────┐
│ Mix the formed suspension and aseptically pass through a        │
│          homogenizer to a sterile holding tank 3.               │
└─────────────────────────────────────────────────────────────────┘
                                ⇩
┌─────────────────────────────────────────────────────────────────┐
│ Pass additional WFI through tank 2 to tank 1 and finally through │
│ homogenizer to sterile holding tank 3 to make up the batch volume. │
└─────────────────────────────────────────────────────────────────┘
```

FIGURE 1

INJECTABLE SUSPENSION COMPRISING AN INSOLUBLE CORTICOSTEROID AND A SOLUBLE CORTICOSTEROID

FIELD OF THE INVENTION

Disclosed herein are processes for the preparation of an insoluble corticosteroid and a soluble corticosteroid suspension, particularly a process for making a betamethasone acetate and a betamethasone sodium phosphate suspension that includes moist heat sterilization and homogenization. The present invention also relates to suspension compositions of an insoluble corticosteroid and a soluble corticosteroid suitable for parenteral administration.

BACKGROUND OF THE INVENTION

Betamethasone acetate and betamethasone sodium phosphate injectable suspension is a formulation containing two synthetic glucocorticoids used for its anti-inflammatory effects in disorders of various organ systems.

Betamethasone acetate is chemically 9-Fluoro-11β,17,21-trihydroxy-16β-methylpregna-1,4-diene-3,20-dione 21-acetate.

Betamethasone sodium phosphate is chemically 9-Fluoro-11β,17,21-trihydroxy-16β-methylpregna-1,4-diene-3,20-dione 21-(disodium phosphate).

The chemical structures for betamethasone sodium phosphate and betamethasone acetate are as follows:

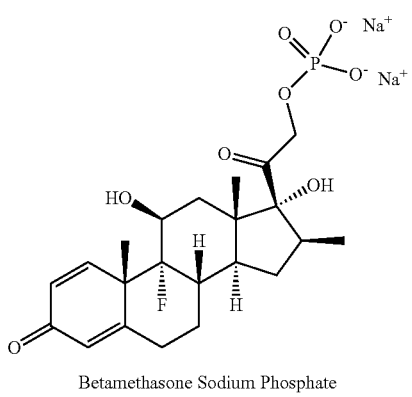

Betamethasone Sodium Phosphate

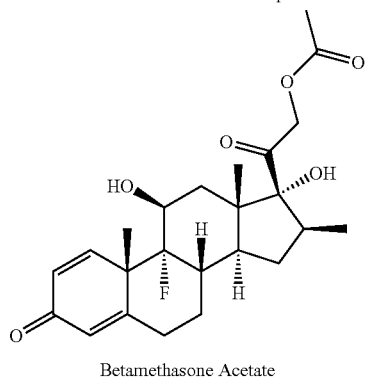

Betamethasone Acetate

Betamethasone sodium phosphate is freely soluble in water and in methanol but is practically insoluble in acetone and in chloroform. In contrast, betamethasone acetate is practically insoluble in water but is freely soluble in acetone and is soluble in alcohol and in chloroform.

Betamethasone is a potent glucocorticoid steroid with anti-inflammatory and immunosuppressive properties. Betamethasone is used to treat the inflammation, swelling, and pain of arthritis. Celestone® Soluspan® (betamethasone injectable suspension) injectable suspension is a sterile aqueous suspension containing 3 mg/mL betamethasone, as betamethasone sodium phosphate, 3 mg/mL betamethasone acetate, 8.9 mg/mL dibasic sodium phosphate dihydrate, 3.8 mg/mL monobasic sodium phosphate dihydrate, 0.1 mg/mL edetate disodium, and 0.2 mg/mL benzalkonium chloride as preservative. The pH is between 6.8 and 7.2. Celestone® Soluspan® is used for intra-articular administration and intralesional administration.

A pharmaceutical suspension is a coarse dispersion in which insoluble solid particles are dispersed in a liquid medium. Suspensions contribute to pharmacy and medicine by supplying insoluble and often distasteful substances in a form that is pleasant to the taste, by providing a suitable form for the application of dermatological materials to the skin and sometimes to the mucous membranes, and for the parenteral administration of insoluble drugs. Pharmaceutical suspensions are often classified into three groups: orally administered mixtures, externally applied lotions and injectable preparations.

Injectable suspension formulations are administered by intravenous (IV), subcutaneous (SC) or intramuscular (IM) routes. Parenteral suspensions are heterogeneous systems that typically consist of a solid phase dispersed in a liquid phase, the liquid phase being aqueous or nonaqueous. To be effective and pharmaceutically acceptable, injectable suspensions should preferably be sterile, stable, resuspendable, syringeable, injectable, isotonic and nonirritating.

A pharmaceutical suspension preparation should possess certain desirable qualities, including the following: i) the suspended material should not settle rapidly; ii) any particles that do settle to the bottom of the container must not form a hard cake but should be readily re-dispersed into a uniform mixture when the container is shaken; and iii) the suspension must not be too viscous to pour freely from the orifice of the bottle or to flow through a syringe needle.

It is important that the characteristics of the dispersed phase be chosen with care so as to produce a suspension having optimum physical, chemical and pharmacological properties. Particle size distribution, specific surface area, inhibition of crystal growth, and changes in the polymorphic form are of special significance and the formulator must ensure that these and other properties do not change sufficiently during storage to adversely affect the performance of the suspensions with aging.

The foregoing characteristics result in manufacturing, storage, and usage requirements that make injectable suspensions one of the most difficult dosage forms to develop.

In the field of injectable preparations, aqueous suspensions for parenteral administration have already been described in scientific and patent literature. These suspensions have been known for a long time and are routinely heat sterilized as ultrafiltration is not a good option; however, autoclave sterilization could result in degradation of the drug.

U.S. Pat. No. 3,962,430 A discloses an autoclaving method for sterilizing active pharmaceutical ingredients in the presence of sodium chloride. This method has been reported to eliminate the problem of change in particle size of betamethasone acetate, dexamethasone acetate, lidocaine hydrochloride, hydrocortisone alcohol, prednisolone tertiary butyl acetate, indomethacin, thiabendazole, testosterone and estradiol.

U.S. Pat. No. 6,495,534 B2 discloses the preparation of stable aqueous suspensions of medroxyprogesterone acetate in a method that utilizes steam sterilization of an aqueous solution of excipients, followed by dispersion of the drug, further homogenization and aseptic filling into the final containers.

U.S. Pat. No. 7,892,483 B2 discloses a process for the sterilization of a steroid that involves heat treating the steroid in the form of a wet mass consisting essentially of the steroid, water and surfactant.

PCT Application Number WO 1999/061001 A1 discloses compositions of submicron to micron sized particles of water-insoluble biologically active substances that are stabilized by thermoprotecting agents and can be terminally steam sterilized without any significant increase of mean particle size.

U.S. Patent Publication Number 2006/0094700 A1 discloses processes for sterilizing a water-insoluble steroid composition comprising heat sterilizing the steroid in the presence of phosphate. The '700 patent publication discloses that the results of the examples show that phosphate salts have an effect on particle size during autoclaving. The phosphate salts decrease the particle size, which the inventors state may be due to the breakup of some crystal aggregates, which is important for injectable suspensions where larger particles sediment rapidly and can contribute to blockage of the fine gauge needle.

PCT Application Number WO 2014/116876 A1 discloses pharmaceutical compositions comprising an insoluble corticosteroid, a soluble corticosteroid and at least one viscosity enhancing agent which provides sustained release delivery. The disclosed insoluble and soluble corticosteroid includes betamethasone among various others.

U.S. Patent Publication Number 2019/0269616 A1 discloses terminal sterilization of a methylprednisolone acetate parenteral suspension by autoclaving at 121° C. for a 45 minute period. Results reported in the patent publication show that there were no changes in methylprednisolone acetate assay values and the level of impurities was not more than 2%, however, there was no information provided on the effect of autoclaving exposure on the particle size of methylprednisolone acetate. The reference also discloses that the drug can be betamethasone acetate.

Thus, there exists an enduring need to develop a robust method for sterilizing a parenteral suspension of an insoluble corticosteroid and a soluble corticosteroid, and which will provide an alternative to existing formulations. The inventors of the present invention have developed a process for preparing a betamethasone acetate and betamethasone sodium phosphate composition comprising moist heat sterilization or autoclaving a slurry of betamethasone acetate in about 30% to about 70% of water to a temperature of about 115° C. to about 128° C. for about 15 minutes to about 60 minutes under nitrogen atmosphere. The suspensions prepared by using the current invention exhibited good physical and chemical stability. Further, suspensions obtained according to the current invention were found to have a similar particle size distribution to that of the reference drug.

SUMMARY OF THE INVENTION

The present invention provides a process for preparation of sterilized suspensions of an insoluble corticosteroid and a soluble corticosteroid composition by moist heat sterilization and homogenization. Particularly, the invention relates to a process for preparation of a sterilized suspension of betamethasone acetate and betamethasone sodium phosphate comprising moist heat sterilization or autoclaving a slurry of betamethasone acetate in about 30% to about 70% of water to a temperature of about 115° C. to about 128° C. for about 15 minutes to about 60 minutes under nitrogen atmosphere.

In another general aspect, there is provided a process for preparation of an insoluble corticosteroid and a soluble corticosteroid suspension composition by moist heat sterilization.

In another general aspect, there is provided a process for preparation of an insoluble corticosteroid and a soluble corticosteroid suspension composition by moist heat sterilization and homogenization.

In another general aspect, there is provided a process for preparation of betamethasone acetate and betamethasone sodium phosphate suspension composition comprising moist heat sterilization or autoclaving a slurry of betamethasone acetate in about 30% to about 70% of water to a temperature of about 115° C. to about 128° C. for about 15 minutes to about 60 minutes under nitrogen atmosphere.

In another general aspect, there is provided a process for preparation of betamethasone acetate and betamethasone sodium phosphate suspension composition comprising moist heat sterilization or autoclaving a slurry of betamethasone acetate in about 30% to about 70% of water at 122° C. in between 15 minutes to 60 minutes under nitrogen atmosphere.

In another general aspect, there is provided a process for preparation of betamethasone acetate and betamethasone sodium phosphate suspension composition for parenteral administration comprising moist heat sterilization or autoclaving a slurry of betamethasone acetate in about 30% to about 70% of water at 122° C. in between 15 minutes to 60 minutes under nitrogen atmosphere.

In another general aspect, there is provided a process that includes a combination of moist heat sterilization for the suspended drug substance and homogenization to formulate betamethasone acetate and betamethasone sodium phosphate having comparable particle size distribution to the reference product.

In one general aspect, there is provided a process for preparation of betamethasone acetate and betamethasone sodium phosphate suspension, wherein the particle size of betamethasone acetate in the suspension ranges from about 0.1 μm to about 30 μm.

In one general aspect, there is provided a process for preparation of betamethasone acetate and betamethasone sodium phosphate suspension, wherein the concentration of betamethasone acetate in a slurry can vary from about 0.1% to about 2.0%.

In one general aspect, there is provided a process for preparation of betamethasone acetate and betamethasone sodium phosphate suspension, wherein the dissolution profile of suspension prepared is identical to the reference product.

In one general aspect, the insoluble form and soluble form of the corticosteroid are in a molar ratio of about 1:1.68.

In one general aspect, the weight ratio of insoluble to soluble corticosteroid may have a range of about 1:1.39.

In one general aspect, there is provided a sterilized injectable suspension composition comprising betamethasone acetate and betamethasone sodium phosphate and pharmaceutically acceptable excipients.

In one general aspect, there is provided a sterilized injectable suspension comprising about 0.3% betamethasone acetate, about 0.3% betamethasone sodium phosphate, about 0.9% dibasic sodium phosphate dihydrate, about 0.4% monobasic sodium phosphate dihydrate, about 0.1% edetate disodium, 0.2% benzalkonium chloride and optionally one or more other pharmaceutically acceptable excipients.

In one general aspect, there is provided a process for preparation of betamethasone acetate and betamethasone sodium phosphate suspension and unit package formulation of the same.

In one general aspect, there is provided a process for preparation of betamethasone acetate and betamethasone sodium phosphate suspension comprising the following steps:

a) In a suitable container, disperse betamethasone acetate in water for injection to form a slurry, sterilize the slurry at a temperature of about 115° C. to about 128° C., more particularly about 122° C., for an appropriate time under nitrogen atmosphere and allow to cool;

b) In another container, prepare a solution of betamethasone sodium phosphate, dibasic sodium phosphate dihydrate, monobasic sodium phosphate dihydrate, edetate disodium, and benzalkonium chloride in water for injection;

c) Transfer the solution of step b) through a 0.22 µm filter to the slurry of step a);

d) Mix the formed suspension and pass through a homogenizer to a sterile holding tank; and e) Pass additional water for injection through the container of step b) to the step a) and finally through a homogenizer to the sterile holding tank to make up the required volume.

In another general aspect, there is provided a process for preparing a sterilized injectable betamethasone acetate and betamethasone sodium phosphate suspension. The suspension is characterized in that the dosage form retains at least 90% w/w of the potency of betamethasone when stored at 25° C. and 60% relative humidity or at 40° C. and 75% relative humidity for 3 months.

In another general aspect, there is provided a process for preparation of betamethasone acetate and betamethasone sodium phosphate suspension, wherein the process is capable of (i) controlling particle size of the betamethasone acetate in a suspension to obtain the desired dissolution profile; (ii) making betamethasone suspensions with variable particle size distributions of betamethasone acetate by varying autoclaving exposure times and homogenization pressure; and (iii) preventing the degradation of betamethasone.

In another general aspect, there is provided a process for preparing a sterilized injectable betamethasone acetate and betamethasone sodium phosphate suspension, wherein the obtained suspension is aseptically distributed into single dose or multidose containers.

In another general aspect, there is provided a process for preparing a sterilized injectable betamethasone acetate and betamethasone sodium phosphate suspension, wherein the obtained suspension can be easily resuspended and easily flows through a syringe needle for intra-articular administration and intralesional administration.

In another general aspect, there is provided a process for preparing a sterilized injectable betamethasone acetate and betamethasone sodium phosphate suspension, wherein the obtained suspension exhibits good stability throughout the shelf life as the impurities observed are well below the specified limits.

BRIEF DESCRIPTION OF THE DRAWING FIGURES

FIG. 1 is a flow chart representation of the manufacturing process of a Betamethasone Sodium Phosphate and Betamethasone Acetate Injectable Suspension.

DETAILED DESCRIPTION OF THE INVENTION

Figure 2:
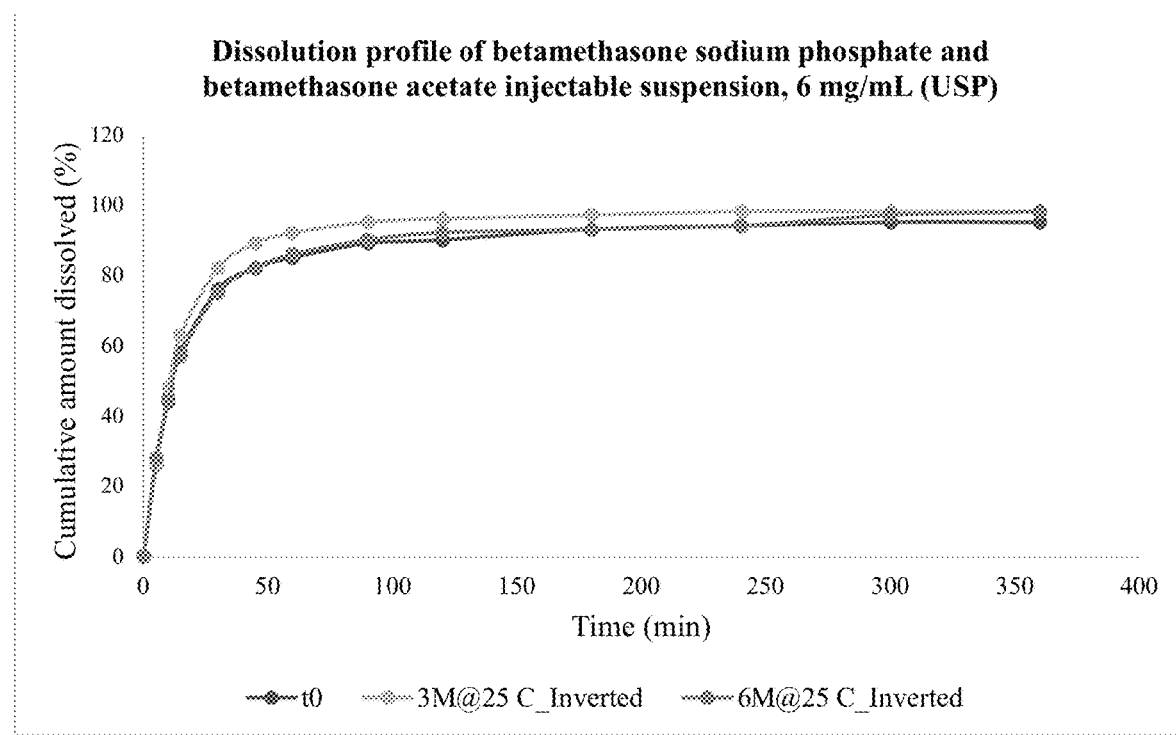
FIG. 2 is a dissolution profile of a formulation prepared according to the present invention and stored at 25° C./60% RH in inverted condition.

The present invention provides a process for preparation of sterilized suspensions of an insoluble corticosteroid and a soluble corticosteroid composition using moist heat sterilization and homogenization. In particular, the invention relates to a process for the preparation of sterilized suspensions of betamethasone acetate and betamethasone sodium phosphate comprising moist heat sterilizing or autoclaving a slurry of betamethasone acetate in about 30% to about 70% of water to a temperature of about 115° C. to about 128° C. for about 15 minutes to about 60 minutes under nitrogen atmosphere.

The insoluble form of the corticosteroid provides a delayed or long-acting effect after being administered to an individual. The insoluble corticosteroid used herein may possess a range of solubility and may exist as a particle in the pharmaceutical formulation. The insoluble corticosteroid is not totally insoluble, but dissolves over time to provide a source of the drug for the individual after the soluble corticosteroid is no longer available. It is understood that the "soluble" and "insoluble" terms as used herein are meant to describe the two forms of the corticosteroid in relative terms and are used to describe forms of the corticosteroids that provide an immediate and delayed effect, respectively, after administration to the individual.

Non-limiting examples of the insoluble corticosteroid are betamethasone acetate, methylprednisolone, prednisolone, triamcinolone acetonide, salts and esters thereof. A specific example is an acetate ester of the corticosteroid. In some embodiments, non-limiting examples of the insoluble corticosteroid include dexamethasone acetate, methylprednisolone acetate, prednisolone acetate, triamcinolone acetonide acetate and dexamethasone.

A soluble form of the corticosteroid provides an immediate or fast-acting effect after being administered to an individual. The soluble corticosteroid may possess a range of solubility, however, it is soluble enough to be dissolved in the pharmaceutical formulation. The solubility of the corticosteroid is determined in part by its chemical form, such as salts or esters. Soluble forms of corticosteroids include salts thereof, such as sodium, phosphate, succinate, and combinations thereof.

Non-limiting examples of soluble corticosteroids include betamethasone sodium phosphate, methylprednisolone sodium succinate, prednisolone sodium succinate, triamcinolone acetonide phosphate ester, and dexamethasone sodium phosphate.

While not intending to limit the scope of the invention in any way, betamethasone acetate is the preferred water-insoluble corticosteroid and betamethasone sodium phosphate is the preferred water-soluble corticosteroid in the compositions prepared according to the present invention.

The ratio of betamethasone acetate and betamethasone sodium phosphate in the suspension is a molar ratio of about 1:1.68. The weight ratio of betamethasone acetate and betamethasone sodium phosphate in the suspension has a range of 1:1.39.

The term "shelf life" refers to the amount of time the suspension composition may be stored without loss of potency and/or dissolution profile. Preferably, the shelf life refers to the amount of time the suspension composition may be stored without a loss of more than 2%, 5%, 8% or 10% of the potency and/or dissolution.

The prepared suspension is suitable for local administration such as intra-articular injection, epidural injection, intra-lesional injection, and intra-ocular injection. The advantages of combining both an insoluble form and a soluble form of a corticosteroid in a pharmaceutical composition for a local injection include: i) The local injection of a soluble form may provide a rapid onset but short duration of action when compared with less soluble preparations; ii) A steroid in a soluble form provides quick action on a target site such as inflamed nerves and tissues, while a steroid in an insoluble form likely becomes available slowly for action while providing a longer lasting effect; and iii) The long-lasting effect may allow a steroid to be injected periodically instead injected daily, which is difficult to do via epidural or intra-articular administration. The pharmaceutical composition of the present application may provide a quick onset of action and a long lasting effect.

The compositions include the betamethasone acetate, betamethasone sodium phosphate and one or more pharmaceutically acceptable excipients selected from the group consisting of preservatives, buffering agents, chelating agents and vehicle.

The preservatives in the suspension compositions are used to inhibit microbial growth and to increase the shelf-life of the composition. Any preservative which does not adversely interact with the active drug or any of the excipients may be employed. Suitable preservatives include, but are not limited to benzalkonium chloride, benzethonium chloride, ethanol, benzyl alcohol, benzoic acid, bronopol, butyl-paraben, cetrimide, and chlorhexidine. The amount of preservative may range, for example, from about 0.01-1%.

The buffering agents or pH-adjusting agent are used in suspension compositions to adjust the pH to a desirable range. Exemplary buffers are well known by those skilled in the art and include acetate, borate, carbonate, citrate, histidine, and phosphate buffers. While not intending to limit the scope of the invention in any way, certain compositions disclosed herein have a pH of from about 6.8 to about 7.2.

Suitable chelating agents include, but are not limited to, metal chelating agents such as, for instance, ethylenediamine tetraacetic acid salts such as edetate disodium.

The vehicle utilized can be an aqueous or non-aqueous vehicle or mixture of aqueous and non-aqueous vehicles.

The osmolality of the suspension is isotonic in a human. The osmolality of the suspension is between 200 mOsm/kg and 350 mOsm/kg, 250 mOsm/kg and 300 mOsm/kg, 280 mOsm/kg and 290 mOsm/kg.

Heating is carried out for the length of time required to kill the pathogens of importance to the application in which the composition is used. Such a determination is well within the skill of a person of ordinary skill in the art. For example, in the compositions herein, the heating is maintained at or near the peak temperature for at least 15 to 60 minutes.

The betamethasone acetate may exist as particles suspended and dispersed throughout the pharmaceutical composition. The particle size of the betamethasone acetate, in combination with other factors such as temperature and composition viscosity, may influence the tendency of the particles to aggregate, settle, or unevenly disperse throughout the pharmaceutical composition. Aggregation of betamethasone acetate particles may change the release profile of the drug. The particle size of betamethasone acetate in the suspension prepared according to the present invention ranges from about 0.1 µm to about 30 µm.

The process for preparing betamethasone acetate and betamethasone sodium phosphate suspension according to the present invention is capable of (i) controlling particle size of betamethasone acetate in a suspension to obtain desired dissolution profile; (ii) making betamethasone acetate suspensions with variable particle size distributions by varying process parameters such as moist heat sterilization, duration of sterilization and homogenization pressure and time; and (iii) preventing the degradation of betamethasone.

It is to be understood that the above description is intended to be illustrative and not restrictive. Many embodiments will be apparent to those of skill in the art upon reading the above description. The scope of the invention should, therefore, be determined with reference to the appended claims, along with the full scope of equivalents to which such claims are entitled. The disclosures of all articles and references, including patents, patent applications and publications, are incorporated herein by reference in their entirety and for all purposes.

EXAMPLE: BETAMETHASONE ACETATE AND BETAMETHASONE SODIUM PHOSPHATE INJECTABLE SUSPENSION COMPOSITION

| Sr. No | Ingredient | Quantity/mL |
|---|---|---|
| 1 | Betamethasone Sodium Phosphate | 3 mg |
| 2 | Betamethasone acetate | 3 mg |
| 3 | Dibasic sodium phosphate dihydrate | 8.90 mg |
| 4 | Monobasic sodium phosphate dihydrate | 3.80 mg |
| 5 | Edetate disodium | 0.10 mg |
| 6 | Benzalkonium chloride | 0.20 mL |
| 7 | Water for injection (WFI) | 1 mL |

Manufacturing Process: The manufacturing process has the following steps:

a) In Tank-1, disperse betamethasone acetate in water for injection, sterilize by moist heat sterilization and allow to cool to room temperature. In one embodiment, the water for injection used is about 30% to about 70% of the total water for injection used in the final composition.

b) In Tank-2, prepare a solution of betamethasone sodium phosphate, dibasic sodium phosphate dihydrate, monobasic sodium phosphate dihydrate, edetate disodium, and benzalkonium chloride in water for injection.

c) Transfer the tank-2 solution through a 0.22 µm filter to tank-1.

d) Mix the formed suspension and pass through a homogenizer to a sterile holding tank (Tank-3).

e) Pass additional water for injection through tank-2 to tank-1 and finally through the homogenizer to the sterile holding tank to make up the volume.

The process variables and particle size distributions (PSD) of betamethasone acetate (BA) in suspension prepared as described in the example are summarized in Table 1.

TABLE 1

| Formulation | BA slurry volume for autoclaving (%) | % of BA in a Slurry | Autoclaving time (min) | Homogenization pressure (PSI) | PSD $D_{10}$ (µm) | $D_{50}$ (µm) | $D_{90}$ (µm) |
|---|---|---|---|---|---|---|---|
| 1 | 70 | 0.43 | 15 | 12500 | 2.21 | 7.96 | 16.0 |
| 2 | 30 | 1 | 15 | 12500 | 2.37 | 8.71 | 17.1 |
| 3 | 50 | 0.6 | 38 | 12500 | 2.02 | 8.11 | 15.7 |
| 4 | 70 | 0.43 | 38 | 20000 | 1.83 | 7.33 | 15.4 |
| 5 | 50 | 0.6 | 60 | 20000 | 1.90 | 7.92 | 16.2 |
| 6 | 30 | 1 | 38 | 5000 | 2.97 | 10.3 | 21.2 |
| 7 | 30 | 1 | 38 | 20000 | 1.84 | 7.54 | 15.5 |
| 8 | 50 | 0.6 | 60 | 5000 | 3.01 | 10.6 | 22.0 |
| 9 | 50 | 0.6 | 15 | 5000 | 3.00 | 10.5 | 21.6 |
| 10 | 30 | 1 | 60 | 12500 | 2.34 | 8.84 | 17.7 |
| 11 | 50 | 0.6 | 15 | 20000 | 1.99 | 7.98 | 16.3 |
| 12 | 70 | 0.43 | 38 | 5000 | 2.73 | 10 | 21.4 |
| 13 | 70 | 0.43 | 60 | 12500 | 2.31 | 8.91 | 17.9 |

Among the various formulations prepared according to the process of the present invention, Formulation #2 exhibited a particle size distribution closer to the reference product. Four replicate batches (R1-R4) of Formulation #2 were prepared and compared for PSD with the reference product. All of the replicate formulations had a PSD comparable to the reference products (RP). The PSD results are summarized in Table 2.

suspension obtained results in the suspension having a similar pharmacokinetic profile in vivo to that of the reference product.

Formulation #2 was subjected to different homogenization pressures to optimize the homogenization pressure and its effect on particle size. The details are summarized in Table 3.

TABLE 3

| Betamethasone acetate slurry volume for autoclaving (%) | Autoclaving time (min) | Homogenization pressure (bar) | Material processed through homogenizer | Particle size distribution (µm) $D_{(v)10}$ | $D_{(v)50}$ | $D_{(v)90}$ |
|---|---|---|---|---|---|---|
| 30 | 15 | 200 | Betamethasone acetate slurry | 2.69 | 9.86 | 19.30 |
|  |  | 400 | Betamethasone acetate slurry | 2.12 | 8.36 | 17.50 |
|  |  | 600 | Betamethasone acetate slurry | 1.85 | 7.60 | 15.70 |
|  |  | 860 | Betamethasone acetate slurry | 1.61 | 6.99 | 14.50 |
|  |  | 1000 | Betamethasone acetate slurry | 1.55 | 6.60 | 13.80 |
|  |  | 200 | Bulk Formulation | 2.67 | 9.31 | 18.30 |

TABLE 2

| Formulation # | Particle Size Distribution (PSD) $D_{10}$ (µm) | $D_{50}$ (µm) | $D_{90}$ (µm) |
|---|---|---|---|
| Formulation# 2 | 2.37 | 8.71 | 17.1 |
| Formulation# 2_R1 | 1.77 | 7.13 | 14.4 |
| Formulation# 2_R2 | 2.27 | 8.55 | 16.5 |
| Formulation# 2_R3 | 1.94 | 7.98 | 15.8 |
| Formulation# 2_R4 | 2.24 | 8.85 | 17.8 |
| RP-Lot #1 | 2.78 | 7.12 | 16.5 |
| RP-Lot #2 | 3.01 | 7.46 | 18.1 |
| RP-Lot #3 | 3.00 | 7.23 | 17.1 |

It was observed from the above results that betamethasone acetate and betamethasone sodium phosphate suspension prepared in accordance with the present invention exhibited a desirable particle size of betamethasone acetate in suspension. The particle size of betamethasone acetate in the suspension is comparable to the reference product. The comparable particle size of betamethasone acetate in the Table 3 reports the optimization of homogenization pressure and was found to be desirable especially at 600 bar.

The physicochemical properties and dissolution profile of this formulation was measured after storing over a period of time. The formulation was tested for stability after storing at 25° C./60% relative humidity. The analytical results are summarized in Table 4 and Table 5, respectively.

TABLE 4

| Time (months) | pH | Betamethasone acetate assay (%) | Betamethasone sodium phosphate assay (%) | Particle size distribution (µm) $D_{(v)10}$ | $D_{(v)50}$ | $D_{(v)90}$ |
|---|---|---|---|---|---|---|
| 0 | 7.09 | 100.4 | 99.2 | 1.84 | 7.31 | 14.70 |
| 3 | 7.11 | 97.4 | 98.5 | 1.84 | 7.27 | 14.90 |
| 6 | 7.18 | 96.9 | 99.8 | 1.85 | 7.06 | 14.50 |

Table 4 summarizes the physicochemical stability data on storage at 25° C./60% RH in an inverted condition. The particle size can be measured using, for example, a Malvern Mastersizer 3000. The particle size results shows that the particle size of betamethasone acetate in the suspension remained within the desirable range and were comparable to the reference product even after storage for six months at 25° C./60% RH in an inverted condition. Further, the assay results show that the suspension remained stable on these storage conditions.

TABLE 5

| Time (min) | Cumulative Amount dissolved (%) | | |
|---|---|---|---|
| | $t_0$ | 3 months | 6 months |
| 0 | 0 | 0 | 0 |
| 5 | 26 | 26 | 28 |
| 10 | 45 | 48 | 44 |
| 15 | 58 | 63 | 57 |
| 30 | 76 | 82 | 75 |
| 45 | 82 | 89 | 82 |
| 60 | 85 | 92 | 86 |
| 90 | 89 | 95 | 90 |
| 120 | 90 | 96 | 92 |
| 180 | 93 | 97 | 93 |
| 240 | 94 | 98 | 94 |
| 300 | 95 | 98 | 97 |
| 360 | 95 | 98 | 98 |

Table 5 summarizes the cumulative release of betamethasone acetate and betamethasone sodium phosphate from suspension prepared in accordance with the present invention at different time intervals, tested after storing the suspension for six months at 25° C./60% RH in inverted condition. The suspension provides drug release entire drugs release in about 6 hours. The dissolution of the composition can be measured using a USP Apparatus IV in a dissolution medium of 0.05% sodium lauryl sulfate (pH 3.0) in a media volume of 500 ml at 37.5° C.±0.5° C.

It should be understood that the above process may be varied. For example, the slurry may consist essentially of, or consist of, the insoluble corticosteroid, betamethasone acetate, and water. The slurry is selected to be suitable for moist heat sterilization. The solution may consist essentially of, or consist of, betamethasone sodium phosphate, water and one or more formulation excipients.

The invention claimed is:

1. A process for preparing a sterile injectable suspension of an insoluble corticosteroid comprising betamethasone acetate and a soluble corticosteroid comprising betamethasone sodium phosphate, wherein the process comprises:
dispersing betamethasone acetate into water to form a slurry;
moist heat sterilizing the slurry of betamethasone acetate in water to form a sterile slurry;
aseptic addition of an aqueous solution comprising betamethasone sodium phosphate and one or more formulation excipients to the sterile slurry; and
homogenization of the aqueous solution and the sterile slurry to form the sterile injectable suspension,
wherein the sterile injectable suspension is not sterilized in a sterilization process that includes a step of a terminal sterilization, the betamethasone acetate in the sterile injectable suspension has a particle size range of from about 0.1 µm to about 30 µm, and the sterile injectable suspension provides entire drug release in about 6 hours.

2. The process for preparation of claim 1, wherein the weight ratio of the betamethasone acetate to the betamethasone sodium phosphate has a range of about 1:1.39.

3. The process for preparation of claim 1, wherein moist heat sterilizing comprises sterilizing to a temperature of about 115° C. to about 128° C. for about 15 minutes to about 60 minutes under a nitrogen atmosphere.

4. The process for preparation of claim 1, wherein the concentration of insoluble corticosteroid in the slurry varies from about 0.1% to about 2%.

5. The process for preparation of claim 1, wherein the sterile injectable suspension comprises about 0.3% betamethasone acetate, about 0.3% betamethasone sodium phosphate, about 0.9% dibasic sodium phosphate dihydrate, about 0.4% monobasic sodium phosphate dihydrate, about 0.01% edetate disodium, about 0.02% benzalkonium chloride and water.

6. The process for preparation of claim 1, wherein the suspension pH is in the range of about 6.8 to about 7.2.

7. The process for preparation of claim 1, wherein the slurry comprises about 30% to about 70% of the water in the sterile injectable suspension.

8. A process for preparing a sterile injectable suspension of betamethasone acetate and betamethasone sodium phosphate, wherein the process comprises:
moist heat sterilizing a slurry of the betamethasone acetate in water to form a sterile slurry;
aseptic addition of an aqueous solution comprising betamethasone sodium phosphate and one or more formulation excipients to the sterile slurry; and
homogenization of the aqueous solution and the sterile slurry to form the sterile injectable suspension, wherein the sterile injectable suspension provides entire drug release in about 6 hours.

9. The process for preparation of claim 8, wherein the weight ratio of betamethasone acetate and betamethasone sodium phosphate has a range of about 1:1.39.

10. The process for preparation of claim 8, wherein the betamethasone acetate particles in the suspension have a D90 value of about 10 µm to about 20 µm.

11. The process for preparation of claim 8, wherein the slurry comprises about 30% to about 70% of water of the sterile injectable suspension.

12. The process for preparation of claim 8, wherein the concentration of the betamethasone acetate in the slurry comprises from about 0.1% to about 2%.

13. The process for preparation of claim 8, wherein moist heat sterilizing a slurry of the betamethasone acetate in water comprises applying a temperature of about 115° C. to about 128° C. for about 15 minutes to about 60 minutes under a nitrogen atmosphere.

14. The process for preparation of claim 8, wherein the betamethasone acetate in the suspension has a particle size range of from about 0.1 µm to about 30 µm.

15. The process for preparation of claim 8, wherein the suspension is not sterilized in a sterilization process that includes a step of a terminal sterilization.

16. The process for preparation of claim 8, wherein the suspension comprises about 0.3% betamethasone acetate, about 0.3% betamethasone sodium phosphate, about 0.9% dibasic sodium phosphate dihydrate, about 0.4% monobasic sodium phosphate dihydrate, about 0.01% edetate disodium, about 0.02% benzalkonium chloride and water.

17. The process for preparation of claim 8, wherein the suspension consists of about 0.3% betamethasone acetate, about 0.3% betamethasone sodium phosphate, about 0.9% dibasic sodium phosphate dihydrate, about 0.4% monobasic sodium phosphate dihydrate, about 0.01% edetate disodium, about 0.02% benzalkonium chloride and water.

18. The process for preparation of claim 8, wherein the pH of the sterile injectable suspension is in the range of about 6.8 to about 7.2.

19. The process for preparation of claim 8, wherein the sterile injectable suspension is suitable for intramuscular and intra-articular use.

20. The process for preparation of claim 1, wherein the sterile injectable suspension consists of about 0.3% betamethasone acetate, about 0.3% betamethasone sodium phosphate, about 0.9% dibasic sodium phosphate dihydrate, about 0.4% monobasic sodium phosphate dihydrate, about 0.01% edetate disodium, about 0.02% benzalkonium chloride and water.

\* \* \* \* \*